United States Patent [19]
Persad

[11] Patent Number: 5,569,278
[45] Date of Patent: Oct. 29, 1996

[54] ARCUATE TONGUE SCRAPER

[76] Inventor: Diane C. Persad, 9701 Elm La., Miramar, Fla. 33025

[21] Appl. No.: 415,244
[22] Filed: Apr. 3, 1995
[51] Int. Cl.$^6$ ..................................... A61B 17/24
[52] U.S. Cl. .............................. 606/161; 15/111
[58] Field of Search ................... 606/161; 15/111

[56] References Cited

U.S. PATENT DOCUMENTS

| | | | |
|---|---|---|---|
| 1,811,775 | 7/1930 | Barkwill | 15/111 |
| 2,049,956 | 8/1936 | Greenberg | 15/111 |
| 2,405,029 | 5/1943 | Gallanty et al. | 15/111 |
| 3,811,447 | 5/1974 | Weber | 606/161 |

FOREIGN PATENT DOCUMENTS 734846  10/1932  France ...................... 15/111

Primary Examiner—Robert A. Hafer
Assistant Examiner—Benjamin K. Koo

[57] ABSTRACT

A scraper for removing debris from a surface of a tongue. The inventive device includes a scraping assembly having a scraping blade for dragging across a surface of a tongue. A handle assembly is pivotally mounted to the scraping assembly and can be stowed for storage and the transportation purposes.

7 Claims, 3 Drawing Sheets

5,569,278

ARCUATE TONGUE SCRAPER

BACKGROUND OF THE INVENTION

1. Field of the Invention

The present invention relates to oral hygiene devices and more particularly pertains to an arcuate tongue scraper for removing debris from a surface of a tongue.

2. Description of the Prior Art

The use of oral hygiene devices is known in the prior art. More specifically, oral hygiene devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art oral hygiene devices include U.S. Pat. No. 5,217,475; U.S. Pat. No. 5,282,814; U.S. Pat. No. 3,683,924; U.S. Pat. No. Des. 324,912; U.S. Design Pat. No. 301,372; and U.S. Pat. No. Des. 291,001.

While these devices fulfill their respective, particular objectives and requirements, the aforementioned patents do not disclose an arcuate tongue scraper for removing debris from a surface of a tongue which includes a scrapping assembly having a scraping blade for dragging across a surface of a tongue, and a handle assembly pivotally mounted to the scrapping assembly which can be stowed for storage and transportation purposes.

In these respects, the arcuate tongue scraper according to the present invention substantially departs from the conventional concepts and designs of the prior art, and in so doing provides an apparatus primarily developed for the purpose of removing debris from a surface of a tongue.

SUMMARY OF THE INVENTION

In view of the foregoing disadvantages inherent in the known types of oral hygiene devices now present in the prior art, the present invention provides a new arcuate tongue scraper construction wherein the same can be utilized for scraping a human tongue. As such, the general purpose of the present invention, which will be described subsequently in greater detail, is to provide a new arcuate tongue scraper apparatus and method which has many of the advantages of the oral hygiene devices mentioned heretofore and many novel features that result in a arcuate tongue scraper which is not anticipated, rendered obvious, suggested, or even implied by any of the prior art oral hygiene devices, either alone or in any combination thereof.

To attain this, the present invention generally comprises a scraper for removing debris from a surface of a tongue. The inventive device includes a scraping assembly having a scraping blade for dragging across a surface of a tongue. A handle assembly is pivotally mounted to the scraping assembly and can be stowed for storage and the transportation purposes.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new arcuate tongue scraper apparatus and method which has many of the advantages of the oral hygiene devices mentioned heretofore and many novel features that result in a arcuate tongue scraper which is not anticipated, rendered obvious, suggested, or even implied by any of the prior art oral hygiene devices, either alone or in any combination thereof.

It is another object of the present invention to provide a new arcuate tongue scraper which may be easily and efficiently manufactured and marketed.

It is a further object of the present invention to provide a new arcuate tongue scraper which is of a durable and reliable construction.

An even further object of the present invention is to provide a new arcuate tongue scraper which is susceptible of a low cost of manufacture with regard to both materials and labor, and which accordingly is then susceptible of low prices of sale to the consuming public, thereby making such arcuate tongue scrapers economically available to the buying public.

Still yet another object of the present invention is to provide a new arcuate tongue scraper which provides in the apparatuses and methods of the prior art some of the advantages thereof, while simultaneously overcoming some of the disadvantages normally associated therewith.

Still another object of the present invention is to provide a new arcuate tongue scraper for removing debris from a surface of a tongue.

Yet another object of the present invention is to provide a new arcuate tongue scraper which includes a scrapping assembly having a scraping blade for dragging across a surface of a tongue, and a handle assembly pivotally mounted to the scrapping assembly which can be stowed for storage and transportation purposes.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
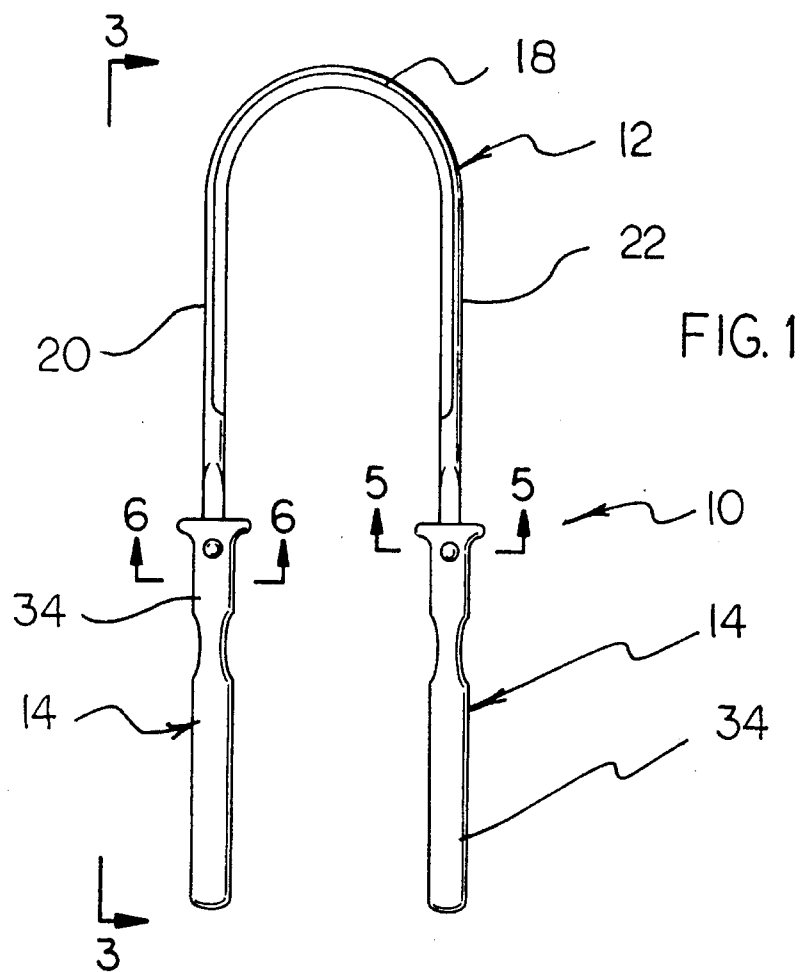
FIG. 1 is a top plan view of an arcuate tongue scraper according to the present invention.

With reference now to the drawings, and in particular to FIGS. 1–6 thereof, a new arcuate tongue scraper embodying the principles and concepts of the present invention and generally designated by the reference numeral 10 will be described.

More specifically, it will be noted that the arcuate tongue scraper 10 comprises a scraping means 12 for engaging an upper surface of a human tongue and scrapping debris, such as plaque and germs, from the upper surface of the tongue. A handle means 14 is pivotally mounted relative to the scraping means 12 for facilitating manual manipulation of the scraping means as desired. By this structure, an individual can manually manipulate the handle means 14 to effect dragging of the scraping means 12 across an upper surface of the tongue to cleanse and remove debris from such tongue.

Figure 2:
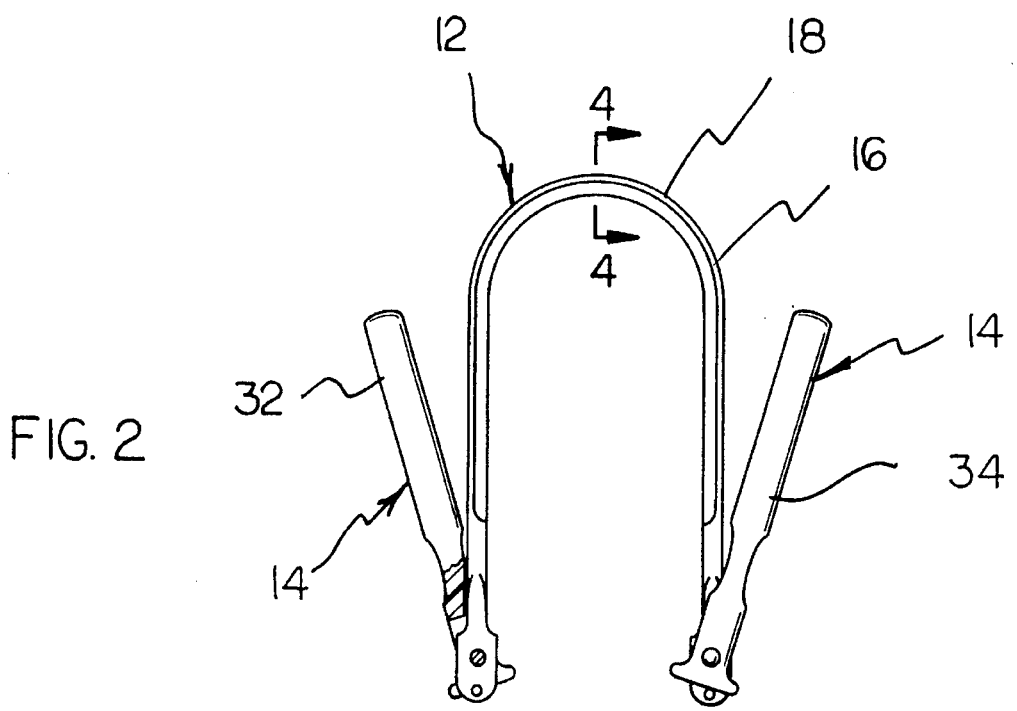
FIG. 2 is a top plan view of invention in a folded configuration.

As best illustrated in FIGS. 1 through 4, it can be shown that the scraping means 12 according to the present invention 10 preferably comprises an arcuate scraping blade 16 including an arcuate scraping leg 18 of substantially semi-circular configuration. A first lateral scraping leg 20 projects from the arcuate scraping leg 18, with a second lateral scraping leg 22 projecting from an opposed end of the arcuate leg and into a substantially spaced and parallel orientation relative to the first lateral scraping leg to define the arcuate scraping blade 16 of the scraping means 12. As shown in the cross sectional illustration of FIG. 4, the scraping legs 18–22 are shaped so as to define a flat engaging surface 24 positionable upon an upper surface of a tongue during use of the device 10. An arcuate outer surface 26 extends from the flat engaging surface 24 and intersects an angled interior surface 28 projecting from the flat engaging surface 24. An intersection of the angled interior surface 28 and the flat engaging surface 24 defines a scraping blade 30 which can be dragged across the upper surface of the tongue to facilitate mechanical removal of debris such as plaque and germs therefrom. The arcuate outer surface 26 serves to provide a smooth outer exterior surface of the arcuate scraping blade 16 which will not damage or traumatize interior surfaces of the mouth during use of the device 10. It should be noted that the specific cross sectional shape illustrated in FIG. 4 of the drawings continues from the arcuate scrapping leg 18 onto the first and second lateral scraping legs 20 and 22 substantially as shown in FIGS. 1 and 2 of the drawings.

Figure 3:
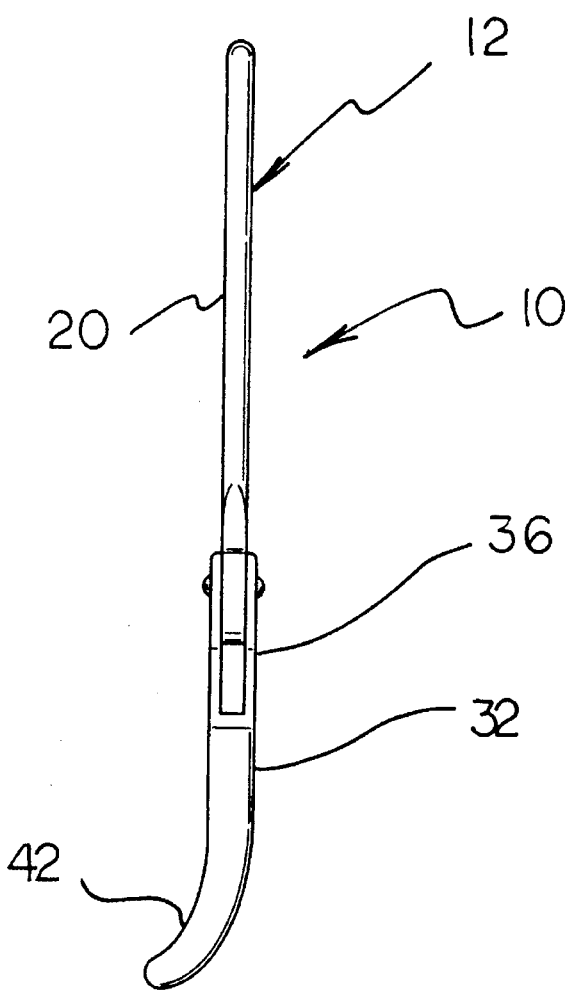
FIG. 3 is a side elevation view taken from line 3—3 of FIG. 1.
Figure 4:
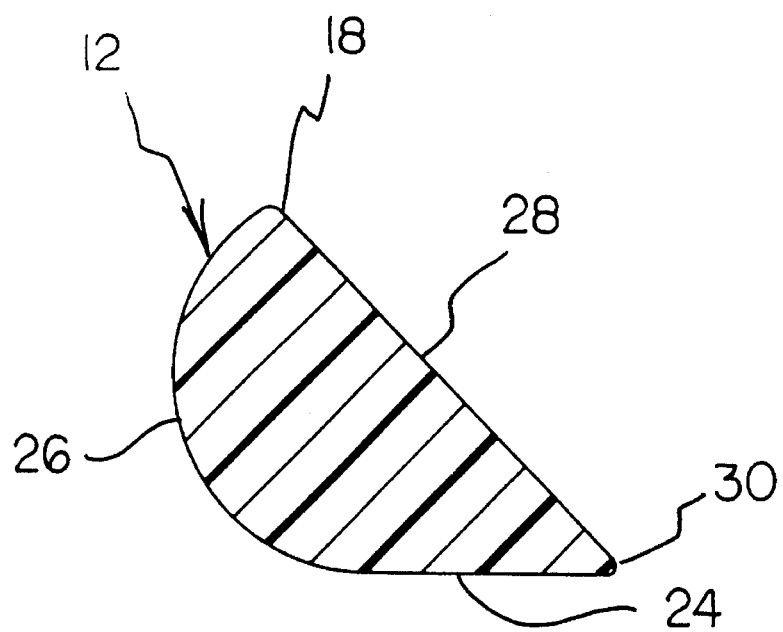
FIG. 4 is a cross sectional view taken along line 4—4 of FIG. 2.
Figure 5:
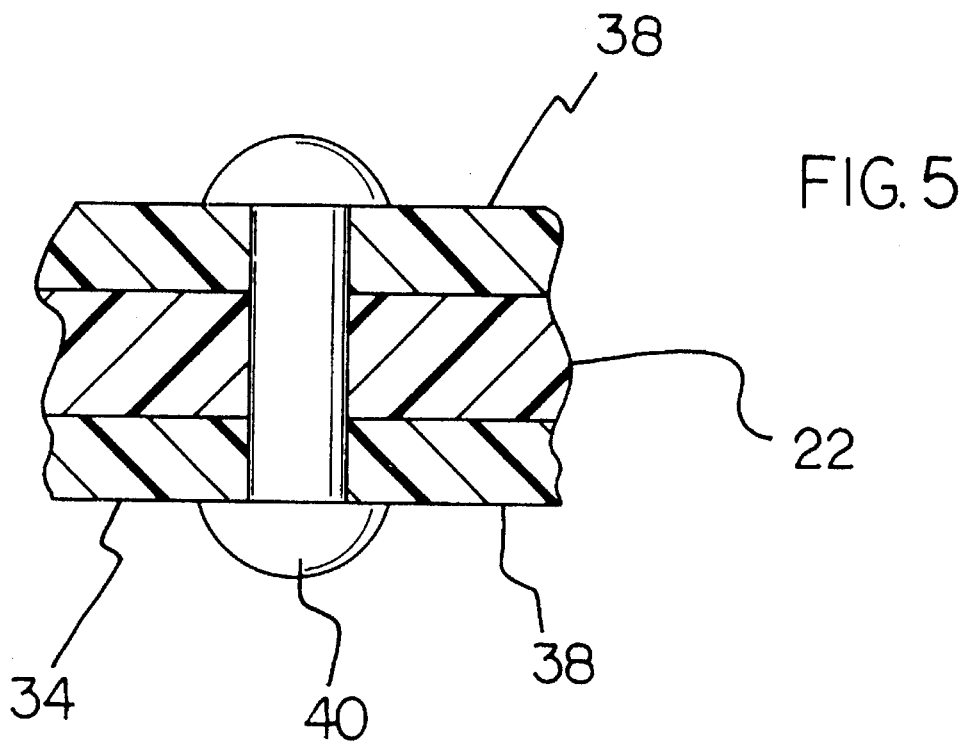
FIG. 5 is a cross sectional view taken along line 5—5 of FIG. 1.
Figure 6:
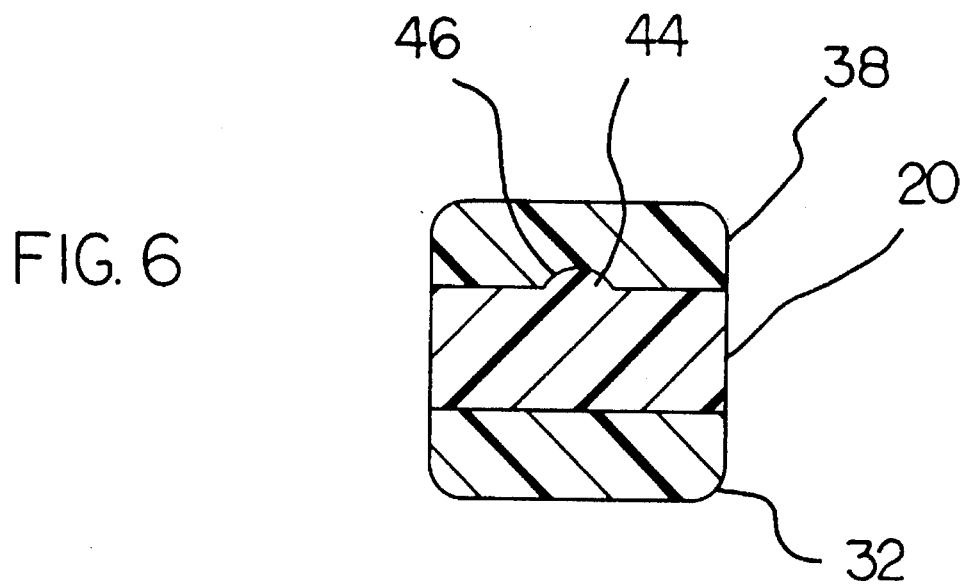
FIG. 6 is a cross sectional view taken along line 6—6 of FIG. 1.

Referring now to FIGS. 5 and 6 with concurrent reference to FIGS. 1 through 3, it can be shown that the handle means 14 according to the present invention 10 comprises a first handle member 32 pivotally mounted to a free distal end of the first lateral scraping leg 20. Similarly, a second handle member 34 is pivotally mounted to the free distal end of second lateral scraping leg 22. To this end and as shown for the first handle member 32 within FIG. 3, each of the handle members 32 and 34 is shaped so as to define a bifurcated end 36 having spaced furcations 38 (see FIG. 5) between which the respective scraping leg 20 and 22 projects. A pivot pin 40 is directed through the furcations 38 of the bifurcated end 36 and through the free distal end of the respective scraping leg 20 or 22 to pivotally mount the respective handle member 32 or 34 relative thereto. Preferably, the handle members 32 and 34 pivot within a plane, with a free distal end of each of the handle members being shaped so as to define an arcuate end 42 projecting from the plane from within which the handle members pivot. The arcuate end 42 serves to engage one or more digits or the human hand during use of the device 10 to facilitate retention of the handle means 14 relative thereto. As shown in FIG. 6 for only the first lateral scraping leg 20, the free distal ends of the scraping legs 20 and 22 are shaped so as to define a detent projection 44 projecting therefrom which is received within a detent notch 46 formed in one of the furcations 38 of the respective handle member 32. The detent projection 44, when received within the detent notch 46 serves to retain the respective handle member 32 or 34 in a desired position relative to the respective scraping leg 20 or 22. Preferably, the handle members 32 and 34 are retained in a substantially collinear orientation relative to the scraping legs 20 and 22 substantially as shown in FIG. 1 of the drawings. By this structure, the handle means 14 permits an individual to easily manipulate the device 10 within a mouth, with the handle members 32 and 34 being pivotally stowed as shown in FIG. 2 for storage and/or transportation purposes.

In use, the arcuate tongue scraper 10 according to the present invention can be easily utilized to facilitate mechanical removal or debris such as plaque or germs from the upper surface of a tongue to improve oral hygiene of an associated individual.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by LETTERS PATENT of the United States is as follows:

1. An arcuate tongue scraper comprising:

a scraping means for engaging an upper surface of a human tongue and scrapping debris therefrom, the scraping means comprises an arcuate scraping blade including an arcuate scraping leg of substantially semi-circular configuration; a first lateral scraping leg projecting from the arcuate scraping leg; and a second lateral scraping leg projecting from an opposed end of the arcuate leg and into a substantially spaced orientation relative to the first lateral scraping leg to define the arcuate scraping blade of the scraping means, the scraping legs so as to define a flat engaging surface positionable upon an upper surface of a tongue; an arcuate outer surface extending from the flat engaging surface; an angled interior surface projecting from the flat engaging surface and intersecting the arcuate outer surface, wherein an intersection of the angled interior surface and the flat engaging surface defines a scraping blade which can be dragged across an upper surface of a tongue to facilitate mechanical removal of debris therefrom;

a handle means pivotally mounted relative to the scraping means for facilitating manual manipulation of the scraping means.

2. The arcuate tongue scraper of claim 1, wherein the handle means comprises a first handle member pivotally mounted to a free distal end of the first lateral scraping leg; and a second handle member pivotally mounted to a free distal end of second lateral scraping leg.

3. The arcuate tongue scraper of claim 2, wherein the handle members are each shaped so as to define a bifurcated end having spaced furcations between which the respective scraping leg projects; and further wherein each of the handle means further comprises a pivot pin directed through the furcations of the bifurcated end and through the free distal end of the respective scraping leg to pivotally mount the respective handle member relative thereto.

4. The arcuate tongue scraper of claim 3, wherein the handle members pivot within a common plane.

5. The arcuate tongue scraper of claim 4, wherein a free distal end of each of the handle members is shaped so as to define an arcuate end projecting angularly from the plane within which each of the handle members pivot.

6. The arcuate tongue scraper of claim 5, wherein the free distal ends of the scraping legs are shaped so as to define a detent projection projecting therefrom; and further wherein one of the furcations of each of the respective handle members includes a detent notch formed therein which receives the respective detent projection to retain the respective handle member in a desired position relative to the respective scraping leg.

7. The arcuate tongue scraper of claim 6, wherein the detent projection cooperates with the detent notch so as to retain the handle members in a substantially collinear orientation relative to the scraping legs.

\* \* \* \* \*